United States Patent [19]

Heine et al.

[11] 4,166,677

[45] Sep. 4, 1979

[54] ILLUMINATION SYSTEM FOR INDIRECT OPHTHALMOSCOPE

[75] Inventors: Helmut A. Heine, Herrsching; Helmut Rosenbusch, Weilheim, both of Fed. Rep. of Germany

[73] Assignees: Propper Manufacturing Co., Inc., Long Island City, N.Y.; Heine Optotechnik GmbH & Co. KG, Herrsching, Fed. Rep. of Germany

[21] Appl. No.: 824,801

[22] Filed: Aug. 15, 1977

[30] Foreign Application Priority Data

Aug. 17, 1976 [DE] Fed. Rep. of Germany ....... 2636977

[51] Int. Cl.² .............................................. A61B 3/12
[52] U.S. Cl. ........................................ 351/16; 351/12
[58] Field of Search .................... 351/16, 12; 362/253, 362/282, 293

[56] References Cited

U.S. PATENT DOCUMENTS

| | | | |
|---|---|---|---|
| 3,019,699 | 2/1962 | Schenk | 351/12 |
| 3,439,978 | 4/1969 | Moore et al. | 351/16 X |
| 3,583,795 | 6/1971 | Heine | 351/16 |
| 3,881,812 | 5/1975 | Ben-Jovim | 351/12 X |

*Primary Examiner*—Paul A. Sacher
*Attorney, Agent, or Firm*—Amster, Rothstein & Engelberg

[57] ABSTRACT

The invention relates to a lighting appliance for generating a light beam for indirect ophthalmoscopy which appliance comprises a housing with a beam outlet aperture through which the beam leaves the housing and first and second means in the housing to respectively modify the color characteristics and the cross-section of the beam leaving the aperture. An externally accessible operating element is provided on the housing which can be independently adjusted to selectively control the first and second means.

10 Claims, 6 Drawing Figures

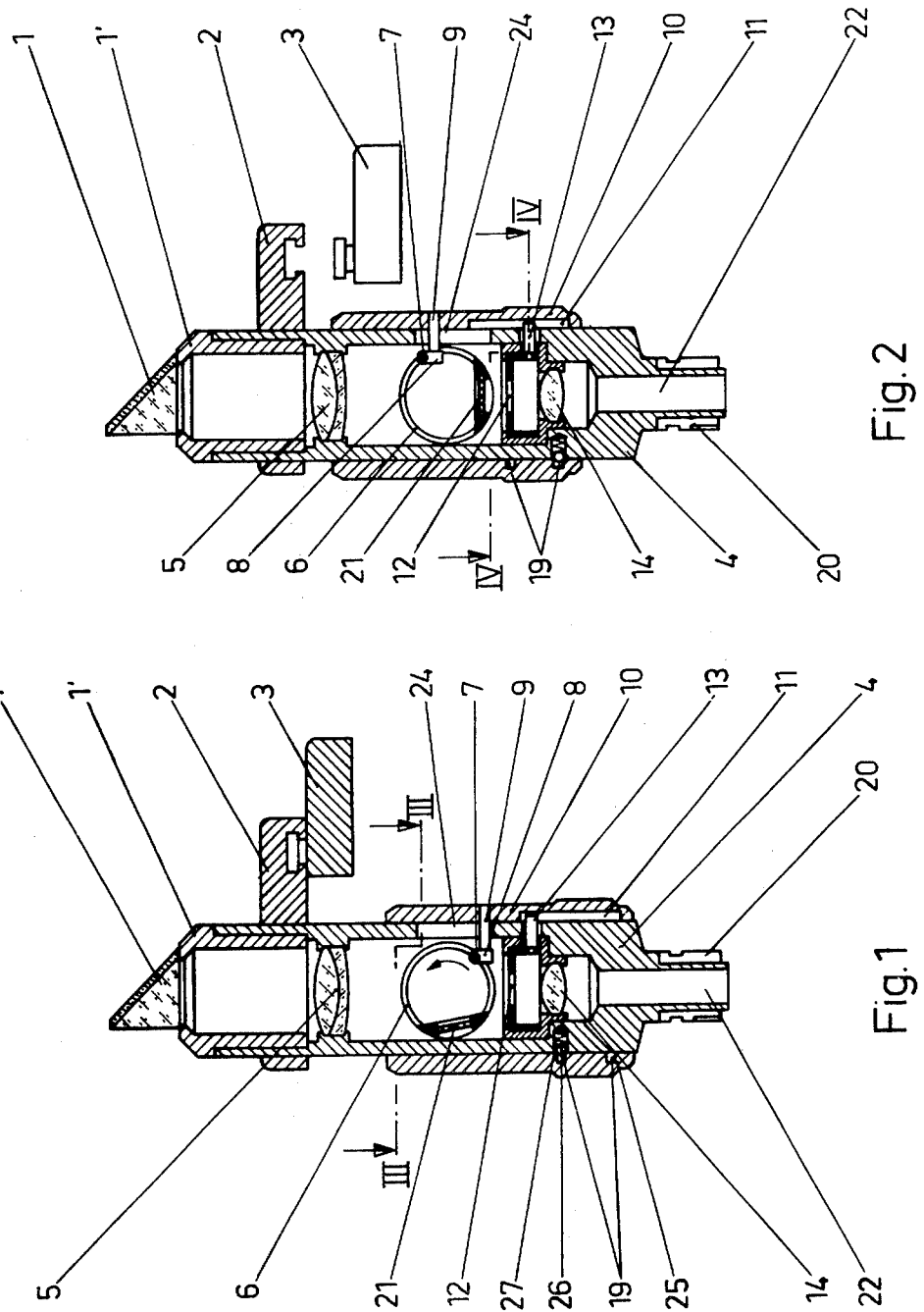

ILLUMINATION SYSTEM FOR INDIRECT OPHTHALMOSCOPE

The invention relates to a lighting appliance for indirect ophthalmoscopy having a housing from which a light beam is emitted, the housing including means to vary the colour of the light beam (e.g. a colour filter) and means to vary the intensity of the light beam (e.g. a diaphragm).

For indirect ophthalmoscopy an ophthalmoscope lens and a separate lighting appliance are necessary. The ophthalmoscope lens is held by the consultant in one hand which he rests against the head of the patient; the other hand holds the lighting appliance in front of the consultant's own eye in such a way that he can look over the edge of the light outlet aperture of the lighting appliance directed onto the patient's eye, at the eye of the patient which is behind the lens of the ophthalmoscope.

The distance between the patient's eye, the lens of the opthalmoscope, the lighting appliance and the consultant's eye are adjusted until the consultant sees the image of the background of the eye, i.e. the retina of the patient, in a clear reverse image.

It is known for the lighting appliance in indirect ophthalmoscopy to be provided with a colour filter, particularly a red-free filter, which can be inserted in the beam path in one way or another; the use of coloured light, particularly red-free light, is very important for diagnosis, in order to make phenomena on the retina of the patient clearer or even simply to enable them to be seen at all. It is also known to use a variable diaphragm to vary the cross-section of the light beam.

Heretofore separate operation of the filter and the diaphragm arrangement has been required so that using the known lighting appliances is not only inconvenient, but in fact the known operating possibilities appear extremely disadvantageous during diagnosis. The consultant must actually remove the lighting appliance and put the opthalmoscope lens down out of his hand in order to be able to effect the necessary adjustments to the lighting appliance. This is not only time-consuming, but disturbs the examination to a considerable extent, since the patient is distracted by these processes and the accommodation of his eye changes, and also the adjustment necessary to obtain a sharp image of the background of the eye must again be tired out, a process which is time-consuming and irksome, even for a practised consultant.

The invention therefore seeks to provide a lighting appliance for the indirect opthalmoscope method with which it is possible to insert the colour filter and diaphragm alternately or both together without having to interrupt the examination process.

This task is solved according to the invention in that the colour and cross-section modifying means are linked to a single operating element in such a way that they can be operated selectively.

With the construction of a lighting appliance according to the invention it is possible to attach the operating element to the housing of the lighting appliance in such a way that it can be moved in the desired direction with one digit of the hand, for example, with the thumb. Preferably, a diaphragm and a colour filter can be operated in this case by displacement or turning of the operating element on the housing of the lighting appliance or also by displacement or turning respectively in two directions.

In a particularly recommended construction form an iris diaphragm can be operated by a turning movement and a colour filter by displacement of the operating element, in a generally cylindrical housing of the lighting appliance. The adjusting pin of the iris diaphragm can be arranged to project through a slit in the form of a segment in the housing, beyond the outer contour of the housing. Further, the filter is mounted in a filter support which can be turned around an axis which is perpendicular to the longitudinal axis of the housing of the lighting appliance. The operating element is in the form of a sleeve which can be turned about and displaced along the housing and a guide groove is provided on the inner surface of the sleeve, running parallel to the longitudinal axis of the housing, into which groove the free end of the adjustment pin of the iris diaphragm can project. The sleeve is also provided with a sliding pin which projects through a longitudinal slit (cut-out) in the housing and is linked to the filter support. With this construction of lighting appliance according to the invention, by displacing the sleeve axially on the housing, the colour filter can be inserted in the path of the beam or removed from it, and by turning the sleeve on the housing the aperture of the iris diaphragm can be altered. Thus, a particularly simple and convenient construction results. Alternatively, several filters could be arranged on a rotatable disc. Instead of an iris diaphragm which can be adjusted continuously, several diaphragms with different diameters could equally well be provided which could be inserted in turn in the path of the beam.

In a construction form which is particularly recommended because it is constructionally simple and easy to manufacture, the filter support is designed as a roller with its ends mounted in the housing of the lighting appliance. In this instance, two holes can be provided, passing through the roller at right angles to its longitudinal axis, in one of which a colour filter is inserted and the other of which allows free passage of the light, the angle between the two openings or bores advantageously corresponding to the relevant terminal position of the roller. Advantageously, however, the roller is equipped with a cut-out which passes through it in the axial direction of the housing and the filter is secured in an opening provided in the wall of the roller casing close to the cut-out.

In this case it is possible to provide a guide pin spanning the cut-out, and to mount a displaceable slide ring on the guide pin with an opening into which the free end of the adjustment pin can project. This constructional form enables a simple connection to be made between the sleeve and the filter support constructed as a roller.

Advantageously, the sleeve is movable between two limit positions in one of which the filter is fully inserted in the path of the beam and in the other of which the beam is unobstructed by the filter. In the case of the turning movements of the sleeve one or more positive location positions can be provided to make it easier to set up specific diaphragm apertures. Naturally, the iris diaphragm can also be set at any intermediate position between the positions of positive location.

In order to provide the consultant with the possibility of holding the lighting appliance as still as possible and in a specific position, a support can be attached to the housing suitably in the vicinity of the outlet aperture where the light beam leaves the housing. Such a support forms a distance spacer which can be rested against the head of the user. It is preferably arranged and constructed in such a way that it can be laid against the lower rim of the orbit (the bony eye-socket). An orbital support can be very important for indirect ophthalmoscopy, since not only must the ophthalmoscope lens be held at the correct distance from the patient's eye, but also the lighting appliance must be held in the hand in such a way that the light beam falls through the lens and the pupil of the patient's eye onto the background of the latter, and the examiner's eye must be brought into that position relative to the lighting appliance, the lens and the patient's eye, which ensures that the examiner actually sees the background of the patient's eye. With an orbital support of the kind described a link is achieved between the examiner's eye and the lighting appliance.

For people who wear spectacles, a normally constructed orbital support is too short since the lighting appliance would lie on the examiner's spectacles. On the other hand, it should be as near as possible to the examiner's eye, so the orbital support cannot be constructed a priori long enough so that both an examiner with perfect vision and also one wearing spectacles can work with it. In order to eliminate this difficulty, an extension piece can be provided for removable connection to the orbital support, for example, by means of a dovetail slot and peg or by means of plug-in pins and corresponding bores.

Preferably, a connecting piece for a handle with a battery compartment or a light-conducting cable will be attached to the housing, and a bore is suitably provided through the connecting piece into the interior of the housing, to take a light-conducting rod or an electric lamp. With a lighting appliance constructed in this way it is possible to connect it as desired to a battery handle or to a so-called cold light projector, i.e., a projector which can be connected via a light-conducting cable to the lighting appliance.

The invention will be described in greater detail, by way of example, with reference to the accompanying drawings, in which:

FIG. 1 is an axial section through a lighting appliance with the filter not inserted and an extension piece fitted to an orbital support.

FIG. 2 is a section similar to FIG. 1 with the filter inserted and the extension piece removed from the orbital support.

Figure 4:
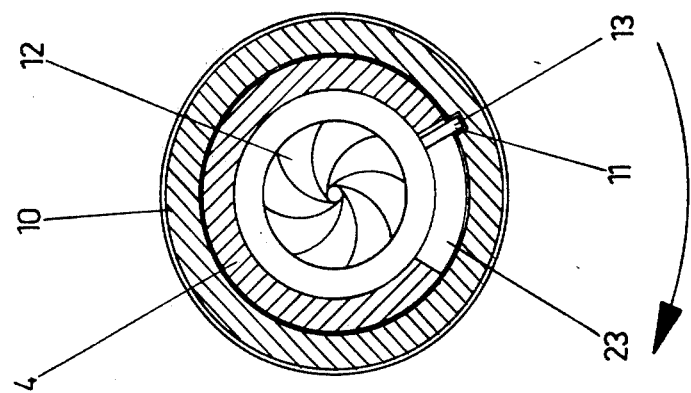
FIG. 4 is the section on the line IV—IV of FIG. 2, showing the diaphragm almost closed.

FIGS. 1 and 2 each show the same longitudinal section through the lighting appliance. As the support for all the components of the lighting appliance there is a cylindrical housing 4 in the upper end of which (as shown in FIGS. 1 and 2) a support 1' for a 90° prism 1 is inserted. Below the support 1' in the interior of the housing 4 there is an illumination lens 5 and below the illumination lens 5 there is a filter support 6 constructed in the form of a roller, mounted by its two ends in the housing wall and bearing a colour filter 21. Below the filter support 6 there is an iris diaphragm 12 and below the diaphragm 12 there is a condenser lens 14 at one end of an axial bore 22. Light from an incandescent lamp (or introduced by means of a light-conducting cable) enters the lighting appliance via the condenser lens 14 and emerges from a light outlet-aperture which is the left-hand surface of the prism 1.

On the other surface of the housing 4 in the vicinity of the light outlet aperture, an orbital support 2 is attached, this projecting from the housing 4 in the direction opposite to that in which light leaves the light outlet aperture, the support 2 being attached to an extension piece 3 by means of a dovetail guide.

Arranged on the housing 4 below the orbital support 2 there is a sleeve 10 which can be turned and also displaced in the axial direction on the housing.

Below the sleeve 10 the housing 4 terminates in a connecting piece 20 for a handle (embodiments of which will be described in more detail in connection with FIGS. 5 and 6). The connecting piece 20 encloses the bore 22 already mentioned.

As shown in FIGS. 1 and 2, the housing 4 is provided with a longitudinal slit 24 through which an adjustment pin 9 projects. The pin 9 can slide in the slit 24 lengthways thereof and is attached to the sleeve 10 so that the filter support 6 can be turned. In FIG. 1 the lighting appliance is shown with the filter 21 not inserted in the light path through the diaphragm 12, whilst in FIG. 2 it is shown with the colour filter 21 inserted in the path of the beam. The change-over is effected by pushing the sleeve 10 upwards and causing the roller-type filter support 6 to turn in the direction of the arcuate arrow shown in FIG. 1.

Figure 3:
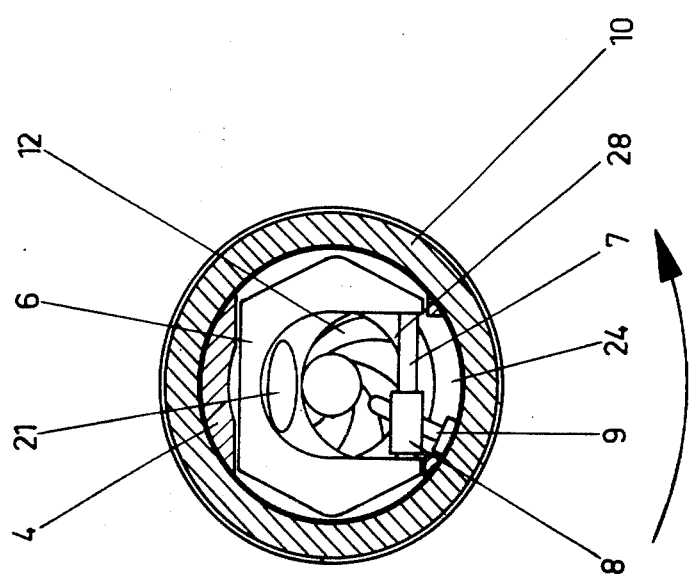
FIG. 3 is the section on the line III—III of FIG. 1, showing the diaphragm open.

The construction of the filter support 6 can be seen in more detail in FIG. 3. As shown, the filter support 6 is mounted by its two ends in the housing 4 and is provided with a cut-out 28 which extends through the support 6 at right angles to the axis about which it turns. In the remaining casing wall of the filter support 6, terminating at the cut-out 28, a hole is provided in which the colour filter 21 is inserted. The open end of the cut-out 28 is spanned by a guide pin 7. Surrounding the guide pin 7 and sliding thereon is a ring 8 which has an opening provided in it through which projects the adjusting pin 9 attached to the sleeve 10. In this way the adjustment sleeve 10 can be turned through an angle which is determined either by the width of the longitudinal slit 24 or by the width of the cut-out 28, depending on whether the housing wall, which terminates at the longitudinal slit 24, or the wall of the roller-type filter support 6 which terminates at the adjustment pin, serve as stops. With this sliding ring 8 design described, the sleeve 10 can be turned without this having any effect on the position of the filter support 6.

Parallel to the longitudinal axis of the lighting appliance, a guide groove 11 is machined in the inner surface of the sleeve 10, and an adjustment pin 13 of the iris diaphragm 12 engages in this groove, this pin 13 projecting through a slit 23 in the housing 4 and in the form of a segment (FIG. 4). The width of the guide groove 11 is only slightly greater than that of the adjustment pin 13. Thus, the aperture width of the iris diaphragm 12 can be varied by turning the sleeve 10 relative to the housing 4.

On the other hand, the aperture width of the iris diaphragm 12 remains unaltered when the sleeve 10 is slid upwards or downwards to change over the filter support 6. FIG. 3 shows the iris diaphragm opened to the maximum, whilst FIG. 4 shows the iris diaphragm almost closed; it can be opened by turning the sleeve 10 in the direction of the arrow shown in FIG. 4 and closed by turning the sleeve 10 in the direction of the arrow shown in FIG. 3. At the lower edge of the sleeve 10 a knurled ring 25 is provided which provides a convenient grip on the sleeve 10. When a handle is actually attached to the connecting piece 20, then the knurled ring 25 can easily be reached with a digit of the hand holding the instrument, and the sleeve 10 can easily be moved upwards or downwards or turned into any desired position.

As shown in FIGS. 1 and 2, two stop grooves 19 which extend over part of the inner circumference of the sleeve 10 are provided on the inner surface of the sleeve 10 and the distance between these grooves 19 equals the length over which the sleeve 10 must be moved in the axial direction of the housing in order to turn the filter support 6 from one to the other of its alternative limit positions. In the housing 4 an appropriate bore is provided, in which a stop spring 27 and a stop ball 26 are located. In this way the sleeve 10 is positively located in its two limit positions so that the position of the filter support 6 will not change during an examination. By means of one or more longitudinal grooves on the inner surface of the sleeve 10 and a further bore with a stop spring and a stop ball (not shown) a similar effect can be achieved with regard to the turning of the sleeve 10, so that the iris diaphragm 12 can be positively held set in one or more specific positions between which intermediate positions are possible as desired. If required, the longitudinal groove 11 can be used as a stop groove for this purpose.

Figure 6:
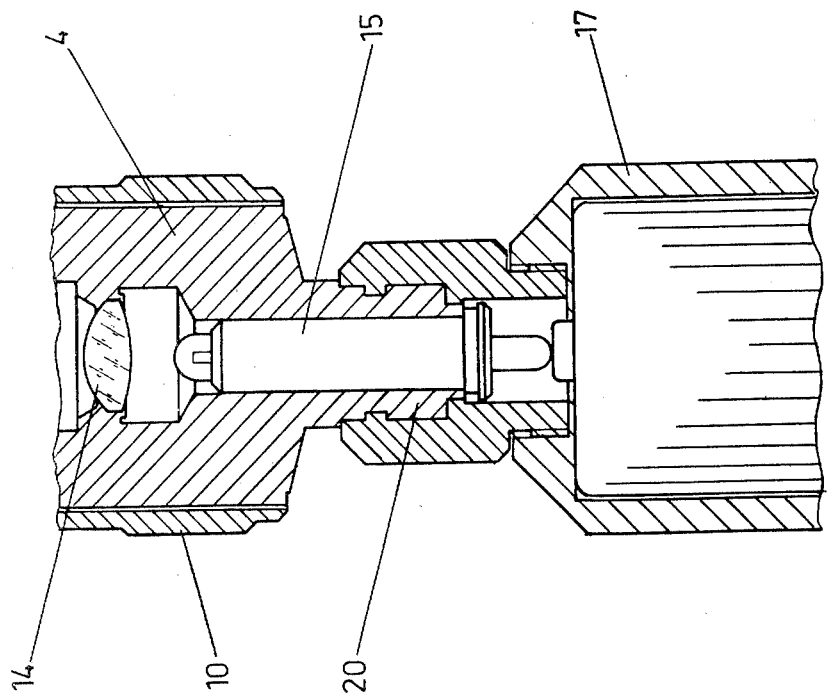
FIG. 6 is a longitudinal section of the lower part of the lighting appliance of FIGS. 1–4 with a handle constructed as a battery container connected to it.
Figure 5:
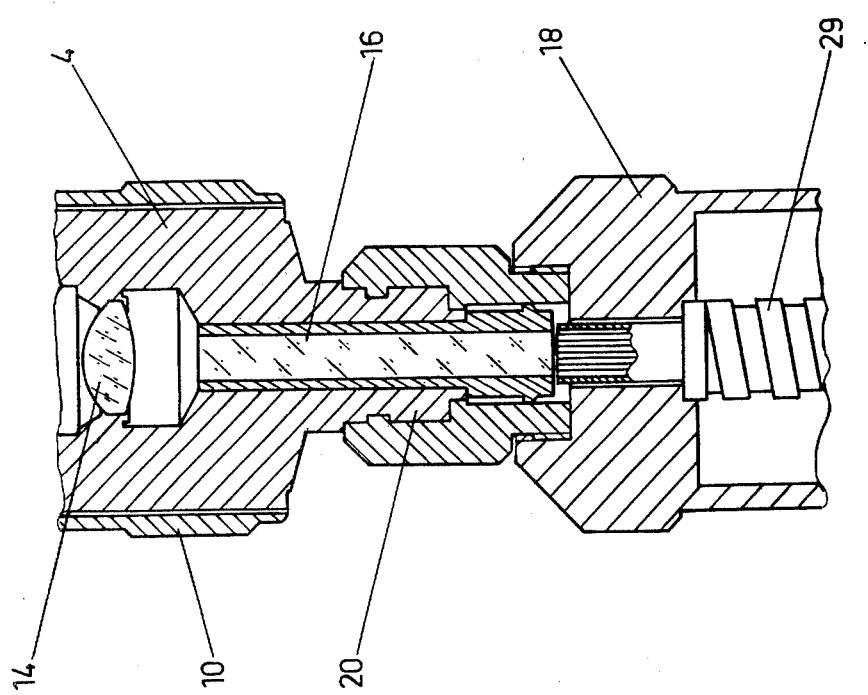
FIG. 5 is a longitudinal section of the lower part of the lighting appliance of FIGS. 1–4 with a handle constructed as a cold light source connected to it.

In FIGS. 5 and 6 the lighting appliance is shown connected to a handle 18 or 17 which is constructed as a holder for a light-conducting cable 29 or as a container for batteries. With the handle 18 constructed as a holder for a light-conducting cable 29, a light-conducting insert 16 is shown inserted in the bore 22 in the housing 4 (FIG. 5), whilst with the construction of the handle 17 as a battery container, a lamp 15 is inserted in the bore 22. In the first case the lighting can be switched on at a cold light projector, which is not shown, and to which the light-conducting cable 29 is connected; in the latter case a switch (not shown) and/or a control resistance is fitted to the handle 17.

In use, the consultant switches the light source on at the cold light projector or at the handle and holds the lighting appliance with one hand in front of his eyes, resting the lighting appliance by its orbital support 2 or the extension piece 3 attached thereto against the lower orbital edge. With the other hand he holds the ophthalmoscope lens in front of the patient's eye which is to be examined, and directs the beam of light emerging from the light outlet aperture into the patient's eye. He can now vary the distance between himself and the patient's eye until he sees the retina of this clearly in a reverse image when he looks over the upper edge of the prism 1 towards the patient's eye. If required, another lens (not shown) can be provided above the light outlet aperture. By turning the sleeve 10, the aperture width of the iris diaphragm 12, and thus the cross-sectional size of the light beam emerging from the lighting appliance, can be optimised to suit the circumstances. By moving the sleeve 10 upwards or downwards, the colour filter 21 can be inserted in the path of the beam or removed from it at will, so that the retina of the patient can be observed in white light or colour modified (e.g. in red-free) light, in order to make special phenomena on the retina visible. All the adjusting movements can be carried out with the one hand holding the lighting appliance, without having to put the lighting appliance down or using the other hand to help in the adjustments.

What is claimed is:

1. An appliance for generating a light beam for indirect ophthalmoscopy comprising a housing, a beam outlet aperture in the housing through which the beam leaves the housing, first means within the housing for varying the colour of the beam leaving the housing and second means within the housing for varying the cross-section of the beam leaving the housing, said first and second means being independently adjustable, and a single operating element associated with both said first means and said second means movable relative to the housing and accessable from outside the housing which independently and selectively adjusts said first means and second means so that said first means and said second means can be operated in conjunction with one another.

2. An appliance according to claim 1, in which the first means is a movably mounted colour filter and the second means is a variable diaphragm and in which one of said means is adjusted by axial displacement of the operating element on the housing and the other said means is adjusted by turning the operating element on the housing.

3. A lighting appliance according to claim 1, in which a support is attached to the housing in the vicinity of the aperture from which the light beam leaves the housing, said support defining a distance spacer adapted to rest against the head of the user.

4. An appliance for generating a light beam for indirect ophthalmoscopy comprising a housing, a beam outlet aperture in the housing through which the beam leaves the housing, an iris diaphragm within the housing having an adjustment pin which projects through a segment shaped slit in the housing beyond the latter, a filter support mounted within the housing to turn about an axis perpendicular to an axial direction of the housing, and a sleeve surrounding the housing serving as an operating element and mounted on the housing for displacement about the axial direction of the housing and turning about that axial direction, the sleeve having on its inner surface a guide groove arranged parallel to the axial direction of the housing, into which groove the free end of the adjustment pin of the iris diaphragm projects, and having a sliding pin attached to the sleeve, projecting through a slit in the housing parallel to the axial direction and connected to the filter support.

5. A lighting appliance according to claim 4, in which the filter support is constructed as a roller mounted by its ends in the housing, with a cut-out extending through it in the axial direction of the housing, and that a colour filter is secured in an aperture formed in a face of the roller casing adjacent to the cut-out.

6. A lighting appliance according to claim 5, in which a guide pin spans the cut-out in the roller and by a member slidable on the guide pin, the slidable member having an opening into which the free end of the sliding pin projects.

7. A lighting appliance according to claim 4, in which the operating element can be moved and/or turned into selected positions at which it is positively located.

8. A lighting appliance according to claim 3, in which a connecting piece for a handle is provided on the housing, a bore being provided through the connecting piece to communicate with the interior of the housing.

9. A lighting appliance according to claim 8, in which the handle defines a battery compartment and the bore contains an electric lamp.

10. A lighting appliance according to claim 8, in which the handle contains a light-conducting cable and the bore contains a light-conducting cable and the bore contains a light-conducting insert.

* * * * *